United States Patent [19]

Wright

[11] 4,324,259

[45] Apr. 13, 1982

[54] BODY FUNCTION DETECTION AND MEDICAL INSTRUMENTS THEREFOR

[75] Inventor: Basil M. Wright, Rickmansworth, England

[73] Assignee: National Research Development Corporation, London, England

[21] Appl. No.: 133,968

[22] Filed: Mar. 26, 1980

[30] Foreign Application Priority Data

May 16, 1977 [GB] United Kingdom .............. 20492/77

[51] Int. Cl.³ ............................................... A61B 5/08
[52] U.S. Cl. ................................................... 128/722
[58] Field of Search ............... 128/634, 653, 659, 721, 128/722, 728, 774, 775, 778, 748

[56] References Cited

U.S. PATENT DOCUMENTS 3,500,826  3/1970  Haire ................................ 128/204.21
3,572,322  3/1971  Wade ................................... 128/722
4,122,837  10/1978  Leonard .............................. 128/774

Primary Examiner—William E. Kamm
Attorney, Agent, or Firm—Cushman, Darby & Cushman

[57] ABSTRACT

It is proposed that respiration in neonates, and respiration and contractions in woman in advanced pregnancy and labour, be detected and measured by direct reference to change of curvature of the abdominal wall during expansion and contraction thereof. An apparatus for this purpose, an abdominal spherometer, comprises a detector capsule having one wall defined by a resilient diaphragm for engagement with the abdominal wall, the capsule being pneumatically connected to a variable volume compartment operably connected, in turn, to a volume-responsive transducer. The compartment is suitably of similar form to the capsule with the transducer being a capacitor having electrodes respectively located as or on the compartment diaphragm and opposite thereto.

6 Claims, 1 Drawing Figure

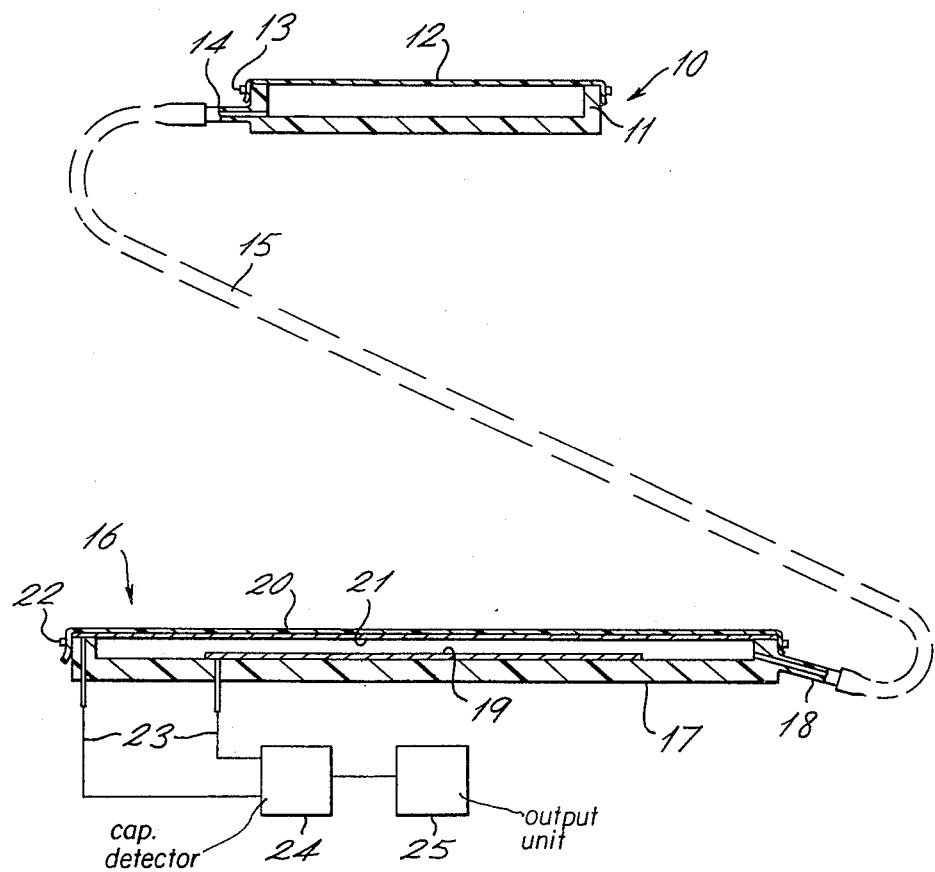

BODY FUNCTION DETECTION AND MEDICAL INSTRUMENTS THEREFOR

This is a continuation, of application Ser. No. 906,351 filed May 15, 1978 now abandoned.

This invention concerns body function detection and medical instruments therefor, and the invention has been conceived initially in connection with the detection and measurement of respiration in neonates.

All of the effective methods of measuring neonatal respiration are unsatisfactory in one way or another because they either involve gross interference with the infant, for example, by intubation, by use of a mask, or by enclosing in a plethysmograph, or they are indirect. An indirect method of detecting neonatal respiration in common usage in the United Kingdom uses detection by way of infant movement on an inflated mattress, but this method gives rise to many false signal outputs and is accordingly unreliable.

The present invention involves a method which can be applied to the detection and measurement of neonatal respiration, and other body functions, in a reliable manner without undue interference with the infant or other patient. This method operates by the detection of change of curvature in the abdominal wall. In the case where the function is neonatal respiration, the method relies on the fact that neonates have soft chests and, in consequence, their respiration is almost purely abdominal, giving a sufficient quantitative relationship between respiratory volume and abdominal expansion for the purposes of clinically useful measurement. In addition, their abdominal walls are very thin, with little or no muscular structure, so that the walls behave like balloons.

A corresponding situation exists in a woman in advanced pregnancy and labour, and it has been found possible to detect respiration and uterine contractions in this case as well by use of the same method.

In order to carry out the proposed method the present invention provides an abdominal spherometer comprising a detector capsule adapted for attachment to the abdominal wall and partly defined by a resilient diaphragm for engagement and complementary movement with such wall when so attached, said capsule being pneumatically connected by flexible tubing to a variable volume compartment which incorporates or is operably connected with a transducer responsive to variations in the volume of said capsule due to abdominal expansion and contraction.

The fact that the transducer is pneumatically connected with and can be located remotely from the detector capsule avoids the hazard which otherwise arises when electrical equipment is engaged directly with, or closely adjacent to the body, and also allows the detector capsule to be of very simple construction and sufficiently small as to be unobtrusive.

A presently preferred form of transducer comprises a capacitor including a fixed electrode and a movable electrode, the latter electrode being in the form of a flexible metallised diaphragm forming a variable wall portion of said compartment.

For a fuller understanding of the present invention, one embodiment of the same is illustrated in partly sectioned manner by the accompanying drawing.

In the drawing the detector capsule is denoted at 10 and has a body 11 of a simple cupped shape which is closed by a diaphragm 12. An overall hollowed disk shape is preferred for compactness, this shape suitably being circular. The body 11 has an overall diameter of about 20 mm and depth of 3 mm, these dimensions having been found suitable for application to neonates. For adults, an increase in diameter up to about 40 mm, and suitably about 30 mm, is appropriate. The body can be made of metal or any suitably rigid plastics material. The diaphragm 12 is made of soft rubber and is secured to the rim of the body by a retaining ring, such as at 13, or by fabrication of the diaphragm in one piece with a moulded ring to seat around the body rim. A nozzle 14 projects from the side of the body to receive one end of a flexible tube 15.

The other end of the tube 15 is similarly connected with a variable volume compartment 16. This compartment is suitably of similar shape and form to the detector capsule, with a unitary body 17 of rigid plastics, electrically insulating material, having a nozzle 18 projecting at the side to receive the tube 15. The base of this body 17 has a thin film of electrically conductive material adhered to its inner face to form a circular disc electrode 19 with an annular region of the base exposed therearound. The compartment 16 is closed by a diaphragm constituted by a sheet 20 of resilient plastics material with a coating 21 of electrically conductive material on one face, this diaphragm being secured to the rim of the component by a retaining ring 22 to form a movable electrode.

The two electrodes of the compartment 16 are connected by individual leads 23 passing through the component 17 to a circuit 24 for measuring and detecting variations in the capacitance defined by the electrodes. The circuit 24 is connected to an output unit 25 which may take a variety of forms for the purposes of display, recording, and/or alarm generation, subject to the function to which the embodiment is applied.

The compartment is suitably of the same order of dimensions as the capsule, this giving a compromise between too small a size for the electrodes to give a readily detectable signal output, and too large an internal volume to give a readily detectable variation in signal output with diaphragm movement.

In initial development the illustrated embodiment has a component 17 about 40 mm is diameter with a fixed electrode of about 25 mm diameter and 0.05 mm inter-electrode spacing, giving a capacitance of about 50 pf when the electrodes are parallel. This embodiment has operated satisfactorily in detecting neonatal respiration to provide an output, by way of a pen recorder, which corresponds well with equivalent outputs from previously existing measuring equipment.

The above-described capacitance tranducer is considered to be particularly advantageous in its constructional simplicity and economy, while providing an operational sensitivity compatible with the detection of neonatal respiration. Thus the transducer compartment is readily made from a moulded component 17 in which the fixed electrode is printed and across which metallised "Melinex" (Registered Trade Mark) is secured and tensioned by a friction-fitted retaining ring to provide the desired inter-electrode spacing automatically. It is to be noted that the presence of any shunting capacitance, such as may arise with a more conventional construction using a metal base component, is avoided.

Notwithstanding a preference for the capacitance transducer in question, other forms of transducer may be employed, such as a variable inductance position transducer connected with a diaphragm of a variable volume compartment.

I claim:

1. An abdominal spherometer comprising:

a detector capsule means adapted for attachment to the abdominal wall and partly defined by a resilient diaphragm for engagement and complementary movement with said wall, said capsule means being in the general form of a hollowed disc with an overall diameter of 20–40 mm;

compartment means enclosing a variable volume;

flexible valveless tube means connecting the interiors of said capsule means and compartment means in continuous mutual communication and defining with said capsule means a closed pneumatic assembly so that the only means of communication between said compartment means and said capsule means is through said flexible valveless tube means;

said compartment means having a movable wall portion;

and a transducer means operably connected with said compartment means to respond to volumetric variations of opposite sense in said capsule means due to abdominal expansion and contraction, said transducer means comprising a capacitor including a fixed electrode and a movable electrode, said movable electrode being a flexible, electrically conductive metallized diaphragm forming said movable wall portion of said compartment means.

2. A spherometer as claimed in claim 1 wherein said capsule means comprises a rigid cup-shaped body having a mouth across which said resilient diaphragm is located.

3. A spherometer as claimed in claim 1 wherein said compartment means comprises a rigid cup-shaped body having a stationary wall portion opposite said movable wall portion, said fixed electrode being carried on said stationary wall portion, and said rigid cup-shaped body of said compartment means being of electrically insulating material, said compartment means being of the same order of dimensions as said capsule means.

4. A spherometer as claimed in claim 1 wherein said diameter is about 30 mm.

5. A spherometer as claimed in claim 1 wherein said disc is about 30 mm thick.

6. The use of an apparatus for monitoring respiration in a neonate:

said apparatus comprising a capsule partly defined by a resilient diaphragm and pneumatically connected by a flexible tube to a variable volume compartment which includes a transducer responsive to variations in the volume of said compartment, said capsule, said tube and said compartment defining a pneumatic circuit closed against the outside atmosphere;

and said use comprising attaching said capsule to said neonate to locate said diaphragm in conforming engagement with his abdominal wall, and locating said compartment remotely from said neonate, said engaged diaphragm undergoing complementary movements with changes in abdominal wall curvature due to respiratory expansion and contraction, said movements causing related volumetric changes in said capsule and, by virtue of said closed pneumatic circuit, corresponding opposite volumetric changes in said compartment, and said transducer responding to these last changes to provide a varying output representing the neonate's respiration.

* * * * *